United States Patent [19]
Deimling et al.

[11] Patent Number: 5,658,538
[45] Date of Patent: Aug. 19, 1997

[54] REACTOR FOR CARRYING OUT GAS-PHASE REACTIONS USING HETEROGENEOUS CATALYSTS

[75] Inventors: Axel Deimling, Neustadt; Uwe Behling, Waldsee, both of Germany

[73] Assignee: BASF Aktiengesellschaft, Ludwigshafen, Germany

[21] Appl. No.: 550,738

[22] Filed: Oct. 31, 1995

[30] Foreign Application Priority Data

Nov. 8, 1994 [DE] Germany ............ 44 39 807.7

[51] Int. Cl.⁶ ...................................... B01J 8/02
[52] U.S. Cl. .................. 422/211; 422/220; 422/222; 422/191; 422/193; 422/201
[58] Field of Search ............... 422/211, 220, 422/221, 222, 191, 192, 193, 201

[56] References Cited

U.S. PATENT DOCUMENTS

| | | | |
|---|---|---|---|
| 2,042,922 | 6/1936 | Beardsley | 23/288 |
| 2,345,423 | 3/1944 | Pfannmüller et al. | 23/288 |
| 3,212,862 | 10/1965 | Christensen | 23/289 |
| 4,714,592 | 12/1987 | Zanma et al. | 422/192 |
| 4,952,375 | 8/1990 | Zardi | 422/148 |
| 5,084,247 | 1/1992 | Heisel et al. | 422/200 |
| 5,110,564 | 5/1992 | Herbort | 422/197 |
| 5,523,061 | 6/1996 | Hoa et al. | 422/191 |

FOREIGN PATENT DOCUMENTS

| | | |
|---|---|---|
| 1426731 | 12/1964 | Germany. |
| 3804390 | 2/1988 | Germany. |
| 90/06807 | 6/1990 | WIPO. |

OTHER PUBLICATIONS

Ullmanns Encyklopadie der technischem Chemie, 1973 Ed. vol. 3, p. 465.

*Primary Examiner*—Christopher Kim
*Attorney, Agent, or Firm*—Keil & Weinkauf

[57] ABSTRACT

Apparatus, in particular reactor for carrying out endothermic catalytically promoted gas-phase reactions, which has, arranged one on top of the other or one inside the other in a common jacket, a tube-bundle heat exchanger 1 consisting of a plurality of parallel tubes provided with baffles 1a securing a flow of the heat exchanging medium in a direction transverse to the axis of said tubes, a reaction space 6 which preferably widens conically upward, has a base and is intended for holding a catalyst bed, a tube-bundle heat exchanger 2 to which material flows laterally and which is provided with baffles 2a, a reaction space 4 which has a base, is closed at the top by a gas dome and is intended for holding a catalyst bed, a central tube 3 for connecting the outer space of the heat exchanger 1 to the gas space above the reaction space 4, and inlet and outlet means for a heating or cooling gas (c) and inlet and outlet means (a or b) for the fresh gas or reaction mixture, respectively.

1 Claim, 1 Drawing Sheet

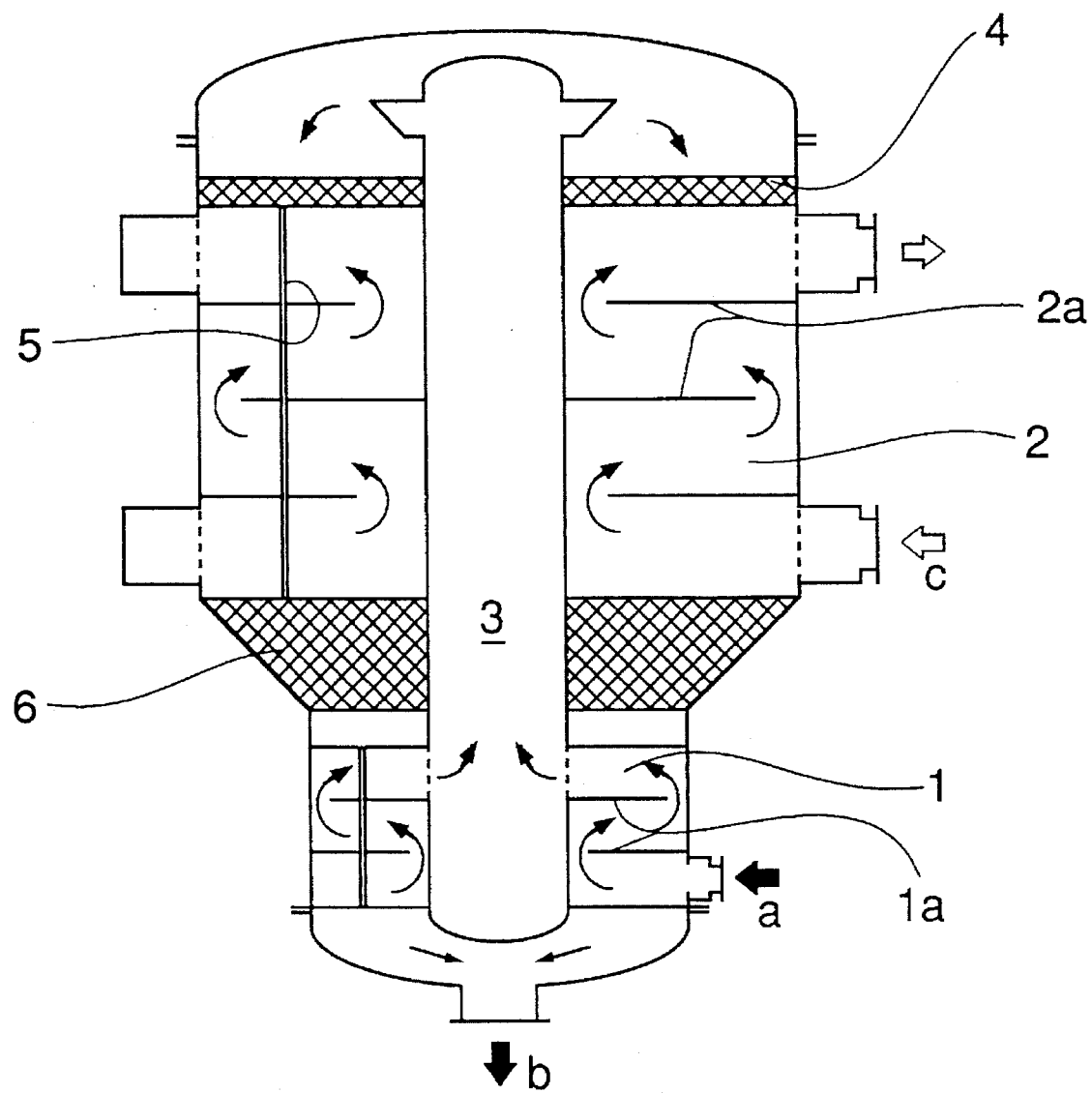

REACTOR FOR CARRYING OUT GAS-PHASE REACTIONS USING HETEROGENEOUS CATALYSTS

In general, fixed bed reactors (axial or radial bed reactors; rack reactors; tube-bundle reactors) are employed industrially for carrying out gas-phase reactions using heterogeneous catalysts (for example formaldehyde, sulfur or styrene synthesis). The supply or removal of the resulting or required heat of reaction in association with such a reactor generally necessitates a relatively large number of heat exchangers. The individual apparatuses are connected to one another by pipelines. A description of the technology is given, for example, in Ullmanns Encyklopädie der technischen Chemie, 1973 edition, Vol. 3, page 465 etc.

This publication discloses the use of apparatuses which are assembled from a plurality of modules and in which, in general at separate points in space, the gases to be reacted are heated up, introduced into a catalyst bed for the reaction and finally cooled again, the heat introduced being used for heating the fresh gases.

According to a proposal unpublished at the priority date of the present invention, a heating gas is first used for heating a tube-bundle reactor which contains a catalyst, for carrying out an endothermic reaction in a reactor consisting of an upper, a middle and a lower part; before the heating gases leave the reactor, however, they are also used for preheating the fresh gas to be reacted, which is effected in a second tube bundle mounted on the reactor. The heating gas is supplied via a central pipe connecting both apparatuses.

The fresh gases in turn are preheated in countercurrent beforehand in a third tube bundle with the reaction products being removed. This third tube bundle forms the lower part of the reaction apparatus; the preheated fresh gases are fed to the stack gas preheater via a fresh gas line which passes along the outside of the apparatus.

This arrangement has disadvantages; in particular, it cannot be constructed in a very compact manner and requires expensive additional insulation of the outer pipe.

It is an object of the present invention to provide an apparatus which has a simple, compact arrangement which requires considerably less capital costs compared with the separate installation and connection of individual apparatuses.

BRIEF DESCRIPTION OF DRAWING

The sole FIGURE is a drawing of the reactor used according to this invention.

DETAILED DESCRIPTION OF DRAWING

The reactor according to the invention is shown in the FIGURE, and can be used for carrying out exothermic or, preferably, endothermic reactions (of the below-mentioned tube bundles, only a single tube is shown in each case). The fresh gas (a) to be reacted is passed radially inward into the jacket space of a tube-bundle heat exchanger 1 which is arranged below the actual reaction apparatus ⅔. In this heat exchanger 1, fresh gas can be preheated by virtue of the fact that the reacted mixture (b) which flows downward through the tubes is cooled. After flowing through the heat exchanger 1, the fresh gas enters a cylindrical inner space 3 arranged concentrically within the reactor itself, through which it is passed upward to the reactor. After deflection, the gas passes via an upstream catalyst bed 4, which may or may not be required, into the catalyst-filled tube of the reaction apparatus 2, in which further heating and the main reaction take place.

In the case of endothermic reactions, the heat of reaction is supplied by a heating gas (c) which is fed countercurrent to the product stream through the jacket space 2 around the tube bundle 5 of the reaction apparatus; if an exothermic reaction is to take place, a cooling medium may be introduced instead. After leaving the tube bundle 5, the reaction mixture is rapidly cooled by being passed through a downstream catalyst bed 6 in which a subsequent reaction can take place. In the subsequent heat exchanger 1, the reaction mixture is cooled while the fresh gas is heated. In the case of exothermic reactions, a further heat exchanger to which the residual heat is fed may be provided.

The reactor according to the invention can accordingly be described in terms of an essentially five-part structure:

The following are arranged one on top of the other in a common jacket

— a tube-bundle heat exchanger 1 consisting of a plurality of parallel tubes provided with baffles 1a securing a flow of the heat exchanging medium in a direction transverse to the axis of said tubes;

— a reaction space 6 which preferably widens conically upward, has a base and is intended for holding a first catalyst bed;

— a tube-bundle heat exchanger 2 to which material flows laterally and which is provided with baffles 2a and has a plurality of individual tubes 5 which can be filled with a catalyst;

— a reaction space 4 which has a base, is closed at the top by a gas dome and is intended for holding a second catalyst bed;

— a central tube 3 for connecting the outer space of the heat exchanger 1 to the gas dome above the reaction space 4;

and inlet and outlet means for a heating or cooling gas (c) and inlet and outlet means (a or b) for the fresh gas or reaction mixture, respectively. Of course, the invention is not restricted to the arrangement including the catalyst filling.

EXAMPLE

For the preparation of styrene, a mixture of steam and ethylbenzene in a weight ratio of 1.25:1 is fed to the catalyst-filled apparatus described above. The total cross-sectional loading in the tube part is 240 kmol/m$^2$h (steam+ethylbenzene). A commercial catalyst of the type G 84 C (manufacturer: Südchemie) is used.

The tubes 5 of the main reactor 2 have an internal diameter of 72 mm and a length of 5500 mm. The height of the bed 6 is 1200 mm and that of the bed 4 is about 500 mm. The jacket diameter of the reactor in the region of the tube bundle 5 is 6800 mm.

An ethylbenzene conversion of 64% is achieved at the lower end of the unheated catalyst bed 6. The styrene selectivity is 95.5 mol %. The pressure at the upper tube base is about 1.8 bar absolute and that after the bed 6 is about 0.5 bar absolute. The temperatures of the catalyst and of the reaction mixture in the apparatus are about 420° C. at the upper tube base (ie. behind the bed 4), about 620° C. at the end of the tube bundle 5 and about 585° C. at the end of the bed 6. The heating gas has a temperature of about 720° C. at the entrance and a temperature of about 500° C. at the exit.

We claim:

1. A reactor for carrying out endothermic or exothermic catalytically promoted gas-phase reactions comprising:

a lower section, a middle section widening ionically upward, and an upper section;

the lower section comprising a first tube-bundle heat exchanger consisting of a plurality of parallel tubes provided with baffles securing a flow of the heat exchanging medium in a direction transverse to the axis of the tubes;

the middle section comprising a first reaction space having a catalyst bed;

the upper section comprising a second tube-bundle heat exchanger consisting of a plurality of parallel tubes provided with baffles securing a flow of the heat exchanging medium in a direction transverse to the axis of the tubes, the second tube-bundle heat exchanger tubes filled with catalyst defining a second reaction space, the upper section further comprising a third reaction space having a catalyst bed;

a central tube extending along the lower section, middle section and upper section, having an inlet in the lower section and an outlet in the upper section;

and an inlet for fresh gas and outlet for reaction mixture in the lower section, and an inlet and outlet for heating or cooling gas in the upper section.

* * * * *